United States Patent [19]

Bennett

[11] 4,170,599

[45] Oct. 9, 1979

[54] PROCESS FOR THE PREPARATION OF 1,3,3-TRIMETHYL-2-OXABICYCLO[2,2,2]OCTAN-6-ONES

[75] Inventor: Gregory B. Bennett, Mendham, N.J.

[73] Assignee: Sandoz, Inc., E. Hanover, N.J.

[21] Appl. No.: 916,867

[22] Filed: Jun. 19, 1978

[51] Int. Cl.$^2$ ............................................ C07D 311/00
[52] U.S. Cl. ................................. 260/345.2; 544/184
[58] Field of Search ...................................... 260/345.2

[56] References Cited

U.S. PATENT DOCUMENTS 3,869,475  3/1975  Mechoulam et al. ............ 260/345.2

Primary Examiner—Nicky Chan
Attorney, Agent, or Firm—Gerald D. Sharkin; Robert S. Honor; Timothy G. Rothwell

[57] ABSTRACT

1,3,3-Trimethyl-2-oxabicyclo[2,2,2]octan-6-ones are prepared by first epoxidizing α-terpineol with a peracid and thereafter oxidizing the resulting product with an appropriate oxidizing agent.

8 Claims, No Drawings

PROCESS FOR THE PREPARATION OF 1,3,3-TRIMETHYL-2-OXABICYCLO[2,2,2]OCTAN-6-ONES

This invention relates to a process for preparing 1,3,3-trimethyl-2-oxabicyclo[2,2,2]octan-6-ones which are useful as intermediates in the preparation of compounds having pharmaceutical activity.

The present invention accordingly provides an improved process for preparing compounds of the formula

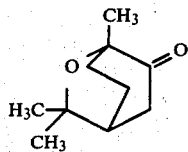

which comprises first epoxidizing a compound of the formula

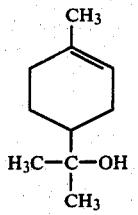

to form an intermediate and thereafter oxidizing said intermediate.

The compounds of formula (I) are prepared first by reacting a compound of the formula (II) with an epoxidizing agent in the presence of an inert atmosphere, e.g., nitrogen, helium or argon and in the presence of an inert organic solvent until a sufficient amount of intermediate is formed. Although the particular epoxidizing agent employed is not critical it is preferred that the reaction be carried out in the presence of a peracid such as peracetic acid, perbenzoic acid or m-chloroperbenzoic acid, the latter being especially preferred. The preferred solvents include the halogenated hydrocarbons such as methylene dichloride, ethylenedichloride, chloroform and the like or the aromatic hydrocarbons such as benzene, toluene and the like or acetic acid, preferably ethylene dichloride. The temperature of the reaction is not critical, but it is preferred that the reaction be run from 0° to 120° C., preferably from about 30° to 90° C. The reaction is typically run from about 1 to 48 hours, preferably from about 8 to 24 hours. The intermediate which is identified as α,α,6-trimethyl-7-oxabicyclo[4,1,0]heptane-3-methanol or 1,3,3-trimethyl-2-oxabicyclo[2,2,2]octan-6-ol, or a mixture thereof is recovered using conventional techniques, e.g., extraction and evaporation. It is preferred, however, that the intermediate be reacted in situ with an oxidizing agent in the presence of an inert organic solvent. Although the particular oxidizing agent employed is not critical, it is preferred that the reaction be run in the presence of pyridinium chlorochromate, or chromium trioxide. If the oxidizing agent is chromium trioxide, the reaction is carried out under aqueous acidic conditions. It is preferred, however, that the oxidation be carried out with pyridinium chlorochromate in the presence of a halogenated hydrocarbon such as methylene dichloride, ethylene dichloride, chloroform and the like, preferably ethylene dichloride. The temperature of the reaction is not critical, but it is preferred that the reaction be run from about 0° to 100° C., preferably from about 20° to 50° C. The reaction is typically run from about 0.5 to 24 hours, preferably from about 1 to 8 hours. The product is recovered using conventional techniques, e.g., extraction and steam distillation.

The compounds of formula (I) are used to prepare the compounds of formula (III) in accordance with the following reaction scheme:

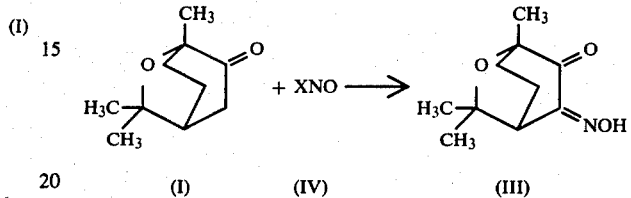

wherein

X represents chloro or lower alkoxy, i.e., alkoxy having 1 to 5 carbon atoms, e.g., methoxy, ethoxy and the like.

The compounds of formula (III) are prepared by nitrosating a compound of the formula (I) with a compound of the formula (IV) in the presence of an inert atmosphere e.g., nitrogen, helium or argon in the presence of an acid catalyst and inert organic solvent. Although the particular acid catalyst employed is not critical, it is preferred that the reaction be carried out in the presence of hydrogen chloride or boron trifluoride etherate, preferably hydrogen chloride. The particular solvent employed also is not critical, however, it is preferred that the reaction be carried out in the presence of an ether such as diethylether, tetrahydrofuran, dioxane and the like, or a halogenated hydrocarbon such as methylene chloride, chloroform and the like, preferably diethylether. The temperature of the reaction is not critical but it is preferred that the reaction be run from about −70° C. to 40° C., more preferably from about −50° C. to 0° C. The product is recovered using conventional techniques, e.g., crystallization.

The compounds of formula (III) are useful as intermediates in the preparation of the corresponding hydrazones in accordance with the following reaction scheme:

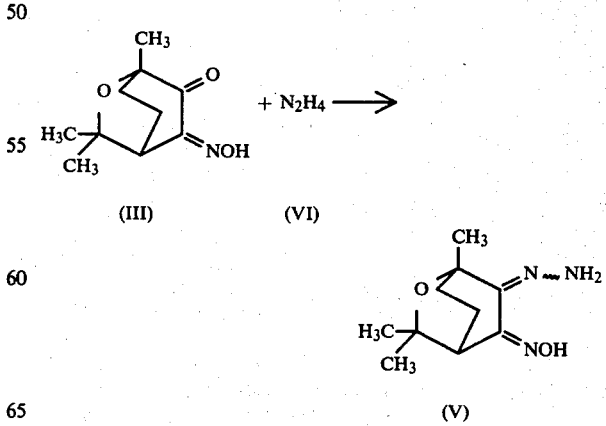

The compounds of formula (V) are prepared by treating a compound of the formula (III) with hydrazine (VI) in an inert atmosphere, e.g., nitrogen, helium or argon, preferably nitrogen in the presence of an inert organic solvent. Although the particular solvent employed is not critical, it is preferred that the reaction be carried out in the presence of the lower alkanols, e.g., methanol, ethanol and the like, preferably ethanol. The temperature of the reaction is not critical, but it is preferred that the reaction be carried out between 0° to 150° C., preferably from about 60° to 110° C. The reaction is run from about 1 to 18 hours, preferably from about 2 to 8 hours. The product is recovered using conventional techniques, e.g., crystallization.

The compounds of formula (V) are useful as intermediates in the preparation of substituted-5,8-dihydro-6,6,8-trimethyl-5,8-ethano-6H-pyrano[4,3-c]-as-triazine-4-oxides in accordance with the following reaction scheme:

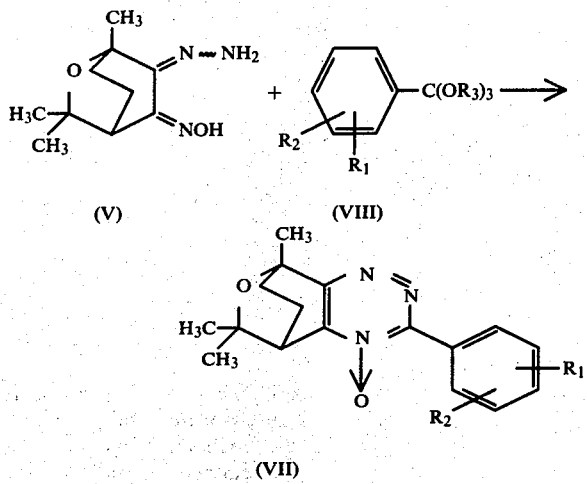

(V)   (VIII)

(VII)

wherein
  R$_1$ and R$_2$ each independently represent hydrogen, halogen having an atomic weight of about 19 to 36, lower alkyl, i.e., alkyl having 1 to 4 carbon atoms, e.g., methyl, ethyl, isopropyl and the like, straight chain lower alkoxy, i.e., alkoxy having 1 to 4 carbon atoms, e.g., methoxy, ethoxy and the like, amino, nitro or trifluoromethyl,
provided that
  (i) when R$_1$ and R$_2$ represent trifluoromethyl, they are on other than adjacent carbon atoms;
  (ii) when R$_1$ and R$_2$ represents t-butyl, they are on other than adjacent carbon atoms; and
  (iii) when one of R$_1$ and R$_2$ is trifluoromethyl and the other is t-butyl, they are on other than adjacent carbon atoms, and
  R$_3$ represents lower alkyl having 1 to 2 carbon atoms, i.e., methyl or ethyl.

The compounds of formula (VII) are prepared by treating a compound of the formula (V) with a compound of the formula (VI) in the presence of an inert atmosphere, e.g., nitrogen, helium or argon and in the presence of an inert organic solvent. Although the particular solvent employed is not critical, the preferred solvents include the aromatic hydrocarbons such as benzene, toluene and the like, the lower alkanols such as methanol, ethanol and the like, or an excess of the ortho ester of formula (VI), the latter being especially preferred. The temperature of the reaction is not critical, but it is preferred that the reaction be run from about 70° to 200° C., preferably from about 130° to 150° C.

The reaction is run from about 12 to 36 hours, preferably from about 15 to 20 hours. The product is recovered using conventional techniques, e.g., filtration.

The compounds of formulae (I), (II), (III), (IV), (VI) and (VIII) are known and may be prepared by methods described in the literature. This invention relates only to the improved process for preparing the known compounds of formula (I).

The compounds of formula (VII) are useful because they possess pharmacological activity animals as sleep inducers and minor tranquilizers as indicated (1) by the hexobarbital reinduction method of Winter, J. Pharmacol. and Exp. Therap., 94, 7–11, 1948; (2) by their ability to produce docility in behavior tests in mice given 10 to 200 mg/kg of animal body weight, i.p. of the test compound according to the 30-word adjective check sheet system basically as described by Irwin S. (Gordon Research Conference, Medicinal Chemistry, 1959) and Chen (Symposium on Sedative and Hypnotic Drugs, Williams and Wilkins, 1954); (3) by their ability to antagonize chronic convulsions and death in mice given 20 to 250 mg/kg i.p. of N-sulfamoylazepine; and (4) by scoring for loss of righting reflex according to the method of Reed-Muench (American Journal of Hygiene, 27: 493–497, 1938), in which mice are administered 12.5 mg/kg. i.p. Thioridazine, immediately after which test compound is administered at dosages of 5 to 100 mg/kg in a volume of 0.1 mg/10 g. body weight. Sixty minutes after dosing, the mice are scored for loss of right reflex.

The sleep inducing effective dosage of the compounds of formula (VII) will vary depending on the particular compound employed. However, in general, satisfactory results are obtained when the compounds are administered orally at a daily dosage of from about 1 milligram to about 75 milligrams per kilogram of animal body weight, typically given in a single dose at bedtime. For most large mammals, the total daily dosage is from about 1 to about 300 milligrams, preferably at bedtime and dosage forms suitable for internal administration comprise from about 0.25 to about 150 milligrams of the compound in admixture with a solid or liquid pharmaceutical carrier or diluent. The preferred pharmaceutical compositions from the standpoint of preparation and ease of administration are solid compositions, particularly hard-filled capsules and tablets.

For minor tranquilizer use, the effective dosage will vary depending on the particular compound employed. However, in general, satisfactory results are obrained when the compounds are administered orally at daily dosage of from about 1.0 milligram to about 75 milligrams per kilogram of animal body weight, typically given in divided doses two to four times per day. For most large mammals, the total daily dosage is from about 5 to 500 milligrams, and dosage forms suitable for internal administration comprise from about 1.25 to about 250 milligrams of the compound in admixture with a solid or liquid pharmaceutical carrier or diluent.

For the uses mentioned above, the compound may be administered orally in such forms as tablets, capsules, elixirs, suspensions and the like, or parenterally in the form of injectable solutions or suspensions. The dosage will vary depending upon the mode of administration utilized and the compound employed.

EXAMPLE 1

1,3,3-Trimethyl-2-oxabicyclo[2,2,2]octan-6-one

A mixture of 3.08 g. (0.02 mole) α-terpineol and 4.45 g. (0.022 mole) of 85 percent m-chloroperbenzoic acid in 70 ml. of ethylene dichloride is refluxed under nitrogen for 20 hours, then cooled to room temperature and washed with aqueous sodium bisulfite and sodium bicarbonate solutions. The solvent is removed in vacuo and the resulting oil is treated in situ with 2.94 g. (0.0136 mole) pyridinium chlorochromate. The resulting mixture is stirred under nitrogen in 35 ml. of methylene chloride at ambient temperatures for 2.5 hours. After addition of 200 ml. diethyl ether, the mixture is filtered through celite and the solvent evaporated to give, on steam distillation, 1,3,3-trimethyl-2-oxabicyclo [2,2,2]octan-6-one; m.p. 50° to 52° C.

EXAMPLE 2

1,3,3-Trimethyl-2-oxabicyclo[2,2,2]octan-5,6-dione-5-oxime

To an ice-cooled solution prepared by adding 50 g. (0.3 mole) 1,3,3-trimethyl-2-oxabicyclo[2,2,2]octan-6-one to a solution of 5 g. of hydrogen chloride gas in 250 ml. diethyl ether is added dropwise 25 ml. of ethylnitrile and after the temperature stabilizes, the mixture is allowed to stand at an ambient temperature for 24 hours, then washed with aqueous sodium bicarbonate solution. After evaporation of the ether, the resulting oil is crystallized from water, yielding 1,3,3-trimethyl-2-oxabicyclo[2,2,2]octan-5,6-dione-5-oxime; m.p. 158°–159° C.

EXAMPLE 3

1,3,3-Trimethyl-2-oxabicyclo[2,2,2]octan-5,6-dione-5-oxime-6-hydrazone

A mixture of 1.97 g. (0.01 mole) 1,3,3-trimethyl-2-oxabicyclo[2,2,2]octan-5,6-dione-5-oxime and 0.35 ml. (0.011 mole) anhydrous hydrazine (98%) in 25 ml. absolute ethanol is refluxed under nitrogen at a bath temperature of 80° C. for 1 hour. After evaporation of the solvent, the residue is recrystallized from ether to give 1,3,3-trimethyl-2-oxabicyclo [2,2,2,]octan-5,6-dione-5-oxime-6-hydrazone; m.p. 138° to 142° C.

EXAMPLE 4

3-Phenyl-5,8-dihydro-6,6,8-trimethyl-5,8-ethano-6H-pyrano [4,3-e]-as-triazine-4-oxide A solution of 2.11 g. (0.01 mole) 1,3,3-trimethyl-2-oxabicyclo[2,2,2]octan-5,6-dione-5-oxime-6-hydrazone in 10 ml. trimethylorthobenzoate is refluxed under nitrogen for 18 hours at a bath temperature of 140° C. during which time all distillate is removed. The resulting mixture is cooled and evaporated to dryness in vacuo. After filtering the residue dissolved in 2% methanol-chloroform through silica gel, and evaporation of the filtrate the resulting solid is triturated with ether, giving 3-phenyl-5,8-dihydro-6,6,8-trimethyl-5,8-ethano-6H-pyrano [4,3-e]-as-triazine-4-oxide; m.p. 186.5° to 189° C.

Following the above procedure and using in place of trimethylorthobenzoate an equivalent amount of
(a) p-chloro-trimethylorthobenzoate,
(b) p-fluoro-trimethylorthobenzoate,
(c) p-methyl-trimethylorthobenzoate,
(d) p-methoxy-trimethylorthobenzoate,
(e) m-trifluoromethyl-trimethylorthobenzoate,
(f) p-amino-trimethylorthobenzoate,
(g) p-nitro-trimethylorthobenzoate,
(h) m-nitro-trimethylorthobenzoate,
(i) m-chloro-trimethylorthobenzoate, or
(j) 3,4-dimethoxy-trimethylorthobenzoate, there is obtained
(a) 3-(p-chlorophenyl)-5,8-dihydro-6,6,8-trimethyl-5,8-ethano-6H-pyrano[4,3-e]-as-triazine-4-oxide,
(b) 3-(p-fluorophenyl)-5,8-dihydro-6,6,8-trimethyl-5,8-ethano-6H-pyrano[4,3-e]-as-triazine-4-oxide,
(c) 3-(p-tolyl)-5,8-dihydro-6,6,8-trimethyl-5,8-ethano-6H-pyrano[4,3-e]-as-triazine-4-oxide,
(d) 3-(p-anisyl)-5,8-dihydro-6,6,8-trimethyl-5,8-ethanol-6H-pyrano[4,3-e]-as-triazine-4-oxide,
(e) 3-(m-trifluoromethylphenyl)-5,8-dihydro-6,6,8-trimethyl-5,8-ethano-6H-pyrano[4,3-e]-as-triazine-4-oxide,
(f) 3-(p-aminophenyl)-5,8-dihydro-6,6,8-trimethyl-5,8-ethano-6H-pyrano[4,3-e]-as-triazine-4-oxide,
(g) 3-(p-nitrophenyl)-5,8-dihydro-6,6,8-trimethyl-5,8-ethano-6H-pyrano[4,3-e]-as-triazine-4-oxide,
(h) 3-(m-nitrophenyl)-5,8-dihydro-6,6,8-trimethyl-5,8-ethano-6H-pyrano[4,3-e]-as-triazine-4-oxide,
(i) 3-(m-chlorophenyl)-5,8-dihydro-6,6,8-trimethyl-5,8-ethano-6H-pyrano[4,3-e]-as-triazine-4-oxide, or
(j) 3-(3,4-dimethoxyphenyl)-5,8-dihydro-6,6,8-trimethyl-5,8-ethano-6H-pyrano[4,3-e]-as-triazine-4-oxide, respectively.

What is claimed is:

1. A process for preparing a compound of the formula

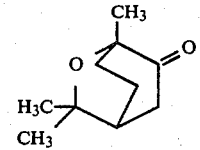

which comprises epoxidizing a compound of the formula

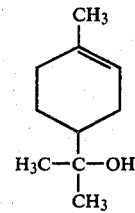

with a peracid under an inert atmosphere in the presence of an inert organic solvent to form an intermediate and thereafter oxidizing said intermediate with pyridinium chlorochromate or chromium trioxide in an inert organic solvent.

2. The process according to claim 1 in which the epoxidation is carried out at a temperature of from 0° to 120° C.

3. The process according to claim 1 in which the epoxidation is run from 1 to 48 hours.

4. The process according to claim 1 in which the epoxidation is carried out under a nitrogen atmosphere.

5. The process according to claim 1 in which the epoxidation is carried out in the presence of an inert organic solvent selected from the group consisting of methylene dichloride, ethylene dichloride and chloroform.

6. The process according to claim 5 in which the inert organic solvent is ethylene dichloride.

7. The process according to claim 1 in which the oxidation is carried out in ethylene dichloride with pyridinium chlorochromate.

8. The process according to claim 1 in which the oxidation is carried out at a temperature of from about 0° to 100° C.

* * * * *